United States Patent
Itsuki et al.

(10) Patent No.: US 8,303,299 B2
(45) Date of Patent: Nov. 6, 2012

(54) ORTHODONTIC IMPLANT STRUCTURE

(75) Inventors: Yasuhiro Itsuki, Tokyo (JP); Norihisa Okada, Tokyo (JP)

(73) Assignees: Yasuhiro Itsuki, Tokyo (JP); Okada Medical Supply Co., Tokyo (JP)

( * ) Notice: Subject to any disclaimer, the term of this patent is extended or adjusted under 35 U.S.C. 154(b) by 102 days.

(21) Appl. No.: 12/524,556

(22) PCT Filed: Jan. 25, 2008

(86) PCT No.: PCT/JP2008/051083
§ 371 (c)(1),
(2), (4) Date: Dec. 30, 2009

(87) PCT Pub. No.: WO2008/090979
PCT Pub. Date: Jul. 31, 2008

(65) Prior Publication Data
US 2010/0112506 A1     May 6, 2010

(30) Foreign Application Priority Data
Jan. 26, 2007  (JP) .................................. 2007-016274

(51) Int. Cl.
*A61C 3/00* (2006.01)
(52) U.S. Cl. ......................................................... 433/18
(58) Field of Classification Search ................. 433/18, 433/173, 174, 20, 22, 24; 623/17.17; 606/280, 606/286, 288, 289, 290, 291
See application file for complete search history.

(56) References Cited

U.S. PATENT DOCUMENTS

| | | | | |
|---|---|---|---|---|
| 4,516,937 A * | 5/1985 | Bosker | ........................... | 433/173 |
| 4,531,917 A * | 7/1985 | Linkow et al. | ................ | 433/176 |
| 4,682,951 A * | 7/1987 | Linkow | ......................... | 433/173 |
| 5,427,906 A * | 6/1995 | Hansen | ......................... | 433/173 |
| 5,567,155 A * | 10/1996 | Hansen | ......................... | 433/172 |
| 5,853,291 A | 12/1998 | DeVincenzo et al. | | |
| 6,302,687 B1 * | 10/2001 | King | ................................. | 433/7 |
| 6,354,834 B2 * | 3/2002 | Kanomi et al. | ................. | 433/18 |
| 6,685,473 B2 * | 2/2004 | Weissman | ..................... | 433/173 |
| 7,431,589 B2 * | 10/2008 | Weissman | ..................... | 433/174 |
| 7,559,764 B2 * | 7/2009 | DeVincenzo et al. | .......... | 433/18 |

(Continued)

FOREIGN PATENT DOCUMENTS

JP     2004-057729     2/2004
(Continued)

OTHER PUBLICATIONS

Office Action for Japanese application No. 2007-016274, mailed Sep. 14, 2010.
(Continued)

*Primary Examiner* — Cris L Rodriguez
*Assistant Examiner* — Eric Rosen
(74) *Attorney, Agent, or Firm* — Nixon Peabody LLP

(57) ABSTRACT

An orthodontic implant structure including: an upper structure body having an insertion hole; a pair of bolts each having a head thread portion, a hexagonal locking portion, an engaging ring, and an embedding thread portion; and a base plate in which are formed a first locking hole and a second locking hole that lock with the hexagonal locking portions and having a projecting thread portion. Both bolts are embedded in bone, the first locking hole is locked on the hexagonal locking portion and a first nut is screwed onto the head thread portion, and the insertion hole is fitted over the projecting thread portion and a second nut is screwed onto the projecting thread portion.

5 Claims, 8 Drawing Sheets

U.S. PATENT DOCUMENTS

| | | | |
|---|---|---|---|
| 7,806,691 B2* | 10/2010 | Berger | 433/172 |
| 2001/0005575 A1* | 6/2001 | Kanomi et al. | 433/18 |
| 2002/0182560 A1* | 12/2002 | Park et al. | 433/18 |
| 2004/0152046 A1* | 8/2004 | Minoretti et al. | 433/173 |
| 2006/0069389 A1* | 3/2006 | Knopfle | 606/61 |
| 2006/0223029 A1* | 10/2006 | Berger | 433/172 |
| 2006/0257811 A1* | 11/2006 | Ohki et al. | 433/18 |
| 2006/0293673 A1* | 12/2006 | Morrison et al. | 606/69 |
| 2008/0124675 A1* | 5/2008 | Adams | 433/174 |
| 2011/0053109 A1* | 3/2011 | Zipprich et al. | 433/18 |

FOREIGN PATENT DOCUMENTS

| | | |
|---|---|---|
| JP | 2005-270175 A | 10/2005 |
| JP | 2006-87932 A | 4/2006 |
| JP | 2006-314419 A | 11/2006 |
| WO | 2006120991 A1 | 11/2006 |

OTHER PUBLICATIONS

International Search Report, PCT/JP2008/051083, dated Feb. 19, 2008.

* cited by examiner

ORTHODONTIC IMPLANT STRUCTURE

CROSS REFERENCE TO RELATED APPLICATIONS OR PRIORITY CLAIM

This application is a national phase of International Application No. PCT/JP2008/051083, entitled "OPTICAL IMPLANT STRUCTURE, which was filed on Jan. 25, 2008, and which claims priority of Japanese Patent Application No. 2007-016274, filed Jan. 26, 2007.

DESCRIPTION

1. Technical Field

The present invention relates to an orthodontic implant structure that is embedded in bone in the mouth to form a fixed base for performing straightening that causes teeth to move.

Priority is claimed on Japanese Patent Application, Publication No. 2007-016274, filed Jan. 26, 2007, the content of which is incorporated herein by reference.

2. Background Art

In the straightening of a row of teeth, conventionally there is an orthodontic method that involves fixing specified teeth, connecting these fixed teeth and teeth that are to be moved (teeth to be straightened), and moving the teeth to be straightened by pulling them. In this case, since the teeth are pulled together, the fixed teeth end up moving as well. Therefore, an orthodontic treatment is performed that consists of embedding a screw-type implant body that forms for example a cylindrical thread portion in the bone of the jaw portion, having this serve as a fixed base, fixing a plate or wire to this implant body with a fixing means (brazing or the like), and fixing the end portion of the plate or wire to a tooth (for example, refer to Patent Document 1).

Patent Document 1 discloses an implant structure that fixes an anchor head that provides a slot at the head portion of the implant body, with a screw hole that passes through this anchor head in the vertical direction being provided. In this structure, the implant body is fixed by being embedded in a jaw bone, a wire having one end fixed to a tooth is engaged in the slot, and by screwing a screw into the screw hole, the wire is fixed at the distal end portion of the screw.

As typical orthodontic implant structures, those that are constituted by screws, and three-point fixing structures are mostly used.

A screw-type implant has a bolt shape with a thread formed on an implant body as disclosed in Patent Document 1 mentioned above, and forms an anchor by screwing the thread portion into bone under a membrane.

On the other hand, a three-point fixing type implant has a structure that is provided with a projecting portion (support portion) that projects out in a direction that is orthogonal to the axial line direction at the distal end portion of the implant. Thereby, by performing a surgical operation to implant the projecting portion into a bone, it is possible to firmly fix it.
Patent Document 1: Japanese Unexamined Patent Application, Publication No. 2004-57729.

BRIEF SUMMARY

Problems to be Solved by the Disclosure

However, conventional implants have the following problems.

A screw-type implant can be readily fixed by rotating a screw without the need for performing a surgical operation. However, the screwed state is inadequate, and during straightening of teeth, when a force acts in the direction of the screw loosening, there is the possibility of the screw loosening, the stability worsening, leading its inability to be used as a fixed base.

Although the three-point fixing implant has a structure that is comparatively harder to come out compared to the screw-type implant, it requires a surgical operation to embed the projecting portion, and has the possibility of taking time for the embedding work.

In light of such circumstances, an implant has been demanded that can be easily implanted without a surgical operation and can also be firmly fixed.

Moreover, since in a conventional implant structure the upper structure body such as a plate or wire is directly fixed to the implant, when performing straightening by exchanging the upper structure body with an upper structure body having a different shape, the implant that has once been embedded must be extracted, and then the new implant must be embedded. Accordingly, there is the possibility of not being able to easily change the upper structure body.

The present invention has as its object to provide an orthodontic implant structure that can be easily embedded without requiring a surgical operation, and that can be firmly fixed with no looseness.

Moreover, the present invention has as the other object to provided an orthodontic implant structure that can cause the upper structure body to be removable without extracting its implant.

Means for Solving the Problem

In order to achieve the abovementioned object, the first aspect of the orthodontic implant structure in accordance with the present invention is an orthodontic implant structure including: an upper structure body having an insertion hole; a pair of bolts of which each bolt has a head thread portion at one end side in the lengthwise axial direction, a locking portion, an engaging portion, and an embedding thread portion at the other end side in the lengthwise axial direction in this order; a base plate that has a projecting thread portion over which the insertion hole can be fitted and a plurality of locking holes, with each of the locking holes capable of allowing insertion of the head thread portion and the locking portion of each bolt but not capable of allowing insertion of the engaging portion, so that by locking with the locking portion is capable of blocking rotation of the locking portion about the lengthwise axial line; first screwing members that can be screwed onto the head thread portions; and a second screwing member that can be screwed onto the projecting thread portion, wherein the locking portions of the pair of bolts to be embedded in the jaw and the locking holes of the base plate are locked, the first screwing members are screwed onto the head thread portions, the insertion hole of the upper structure body is fitted over the projecting thread portion of the base plate, and the second screwing member is screwed onto the projecting thread portion.

In the present invention, the base plate is disposed by locking the locking holes of the base plate on the locking portions of the pair of bolts that have been embedded, and by screwing the first screwing members onto the head thread portions of both bolts, fitting the insertion hole of the upper body structure over the projecting thread portion of the base plate, and screwing the second screwing member onto the projecting thread portion, the upper structure body can be fixed in the mouth. Since the locking portions of the pair of bolts, by having a predetermined shape, are made to lock in the locking holes of the base plate, rotation of the pair of bolts with respect to the base plate is restricted, whereby they are firmly fixed without coming loose. Since the upper structure body can be attached and detached from the base plate by removing the second screwing member, when for example it is desired to move a tooth by pulling it in a different direction, it is possible to perform straightening of teeth by exchanging the upper structure with an upper structure body that has a different shape. Also, by providing the engaging portion at the upper portion of the embedding thread portion of the bolt, it is possible to prevent the head portion of the bolt from sinking into the membrane.

It is preferable that the cross section of the locking portion that is perpendicular to the lengthwise axial direction has a polygonal shape.

Also, it is preferable that the engaging portion has a cross section of a size that can encompass the circumscribed circle of the polygonal shape of the locking portion.

Furthermore, it is preferable that at least one locking hole has a hole cross-sectional shape that is complementary to the polygonal shape of the locking portion.

It is preferable that at least one locking hole has an elongated hole shape that extends in the direction approximately perpendicular to the lengthwise axial line direction. In this case, it is possible to lock the locking portion of one bolt in the locking hole of the base plate which is not the elongated hole, and lock the locking portion of the other bolt within the range of the elongated hole (locking hole) of the other bolt. For that reason, even for example if the distance between the pair of bolts is in a state of not being constant or in a state of not being mutually parallel, for example, since it is possible to dispose/fix the base plate on the pair of bolts in the range of the elongated hole smoothly, work to embed the bolts at a high accuracy becomes unnecessary, and simplification of the work can be achieved.

Effect of the Invention

According to the orthodontic implant structure of the present invention, it is possible to restrict rotation of the bolts by causing the locking holes of the base plate to lock with the locking portions of the pair of bolts, the bolts do not slip out and loosen, and it is possible to firmly fix the bolts to a bone in the mouth. Since the implanted bolts do not wobble, it is possible to prevent the first screwing members that are screwed onto the head thread portion from loosening. Moreover, by being an implant structure that does not require a surgical operation, the bolts can be readily embedded simply by screwing in with rotation.

Also, in this implant structure, it is possible to exchange only the upper structure body without removing the bolts that have once been embedded. Accordingly, it is possible to exchange the upper structure body with a suitable upper structure body depending on the teeth straightening method such as changing the direction of pulling the teeth, and so it becomes possible to move teeth in various directions with respect to the teeth being straightened, and suitable and reliable treatment can be performed.

The abovementioned and other objects, operations and effects of the present invention would be evident to a person skilled in the art from the appended drawings and the detailed description of the embodiments of the present invention.

DETAILED DESCRIPTION

Hereinbelow, the first embodiment of the orthodontic implant structure of the present invention will be described in detail with reference to FIG. 1 to FIG. 4.

Figure 1:
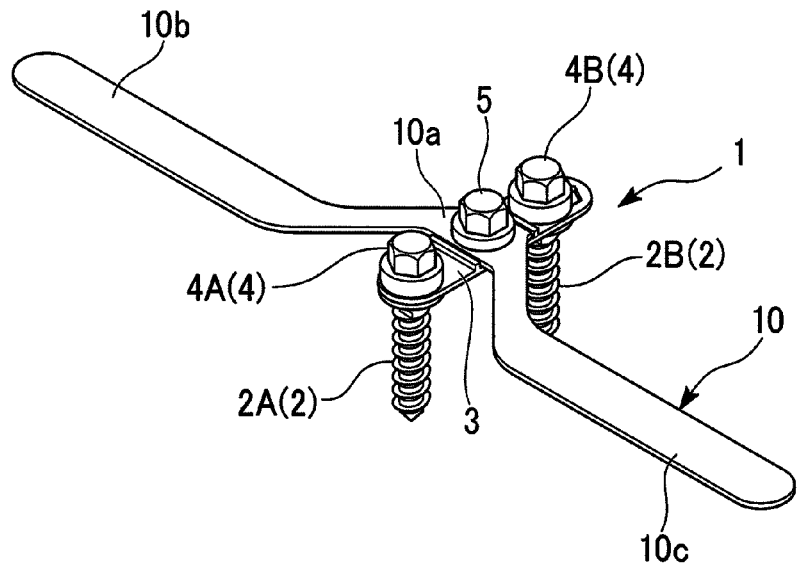
FIG. 1 is a perspective view of the implant structure in accordance with the first embodiment of the present invention.
Figure 2:
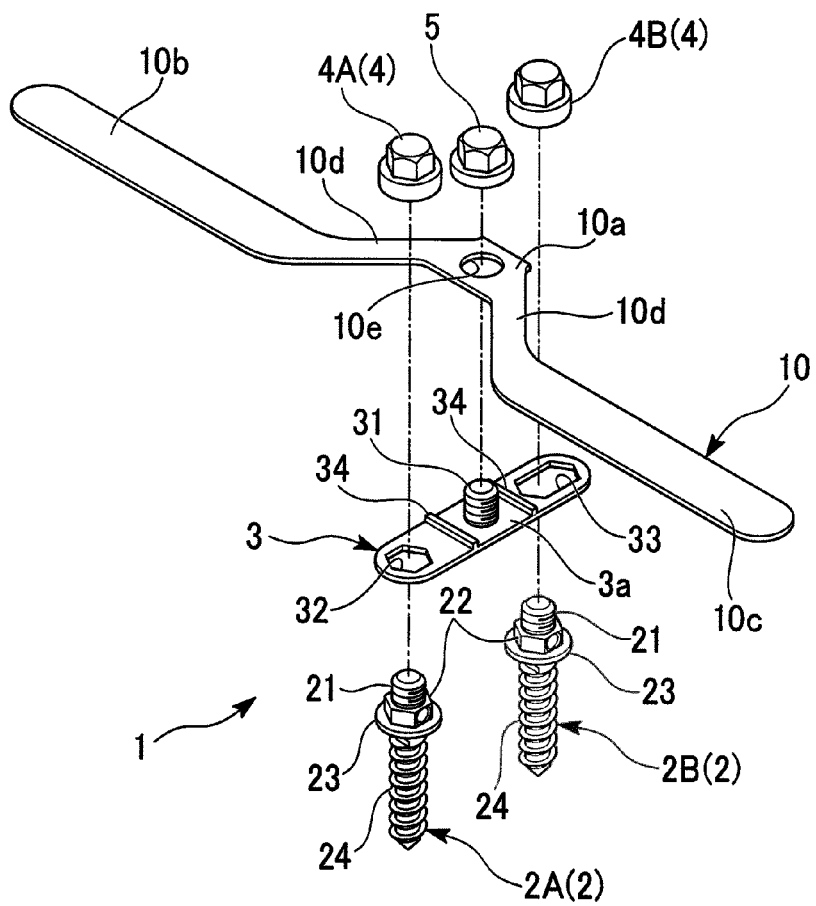
FIG. 2 is an exploded perspective view of the implant structure shown in FIG. 1.
Figure 3A:
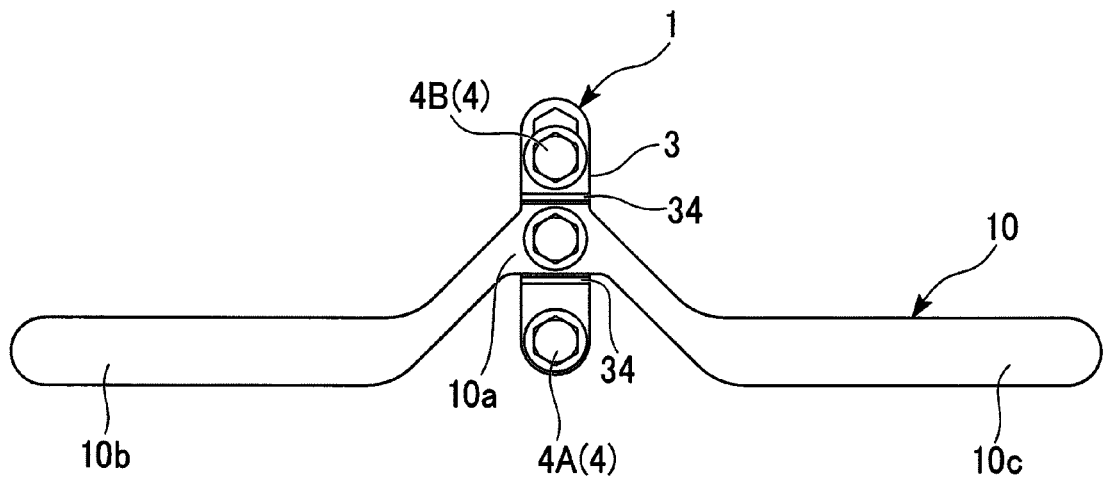
FIG. 3A is a plan view of the implant structure shown in FIG. 1.
Figure 3B:
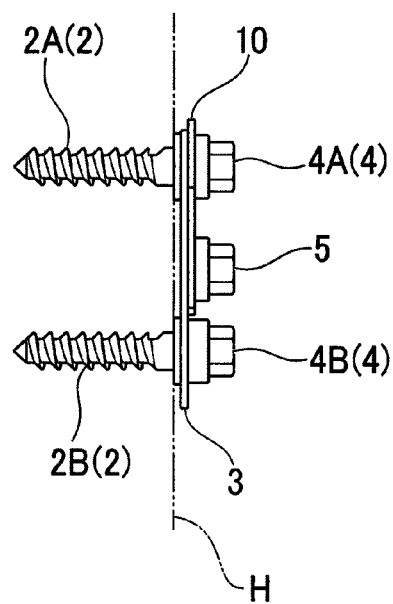
FIG. 3B is an elevation view of the implant structure shown in FIG. 1.
Figure 4:
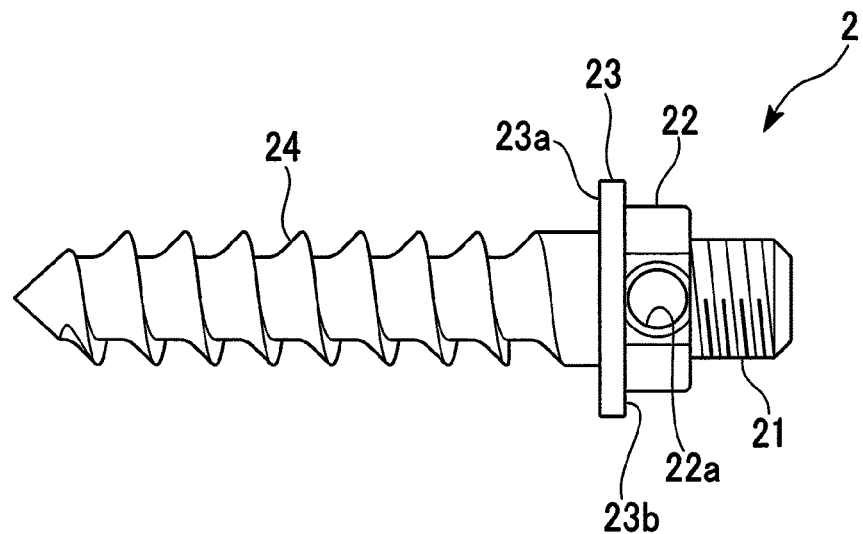
FIG. 4 is an elevation view of the bolt.

FIG. 1 is a perspective view that shows the implant structure in accordance with the first embodiment of the present invention, FIG. 2 is an exploded perspective view of the implant structure shown in FIG. 1, FIG. 3A and FIG. 3B are drawings that show the implant structure, with FIG. 3A being a plan view and FIG. 3B being an elevation view, and FIG. 4 is an elevation view of the bolt.

As shown in FIG. 1, the orthodontic implant structure in accordance with the first embodiment is used for moving a tooth in a predetermined direction by embedding bolts 2 in a jaw bone in the mouth to fix them, fixing an upper structure body 10 to the head portion of these bolts 2 to arrange it in the mouth, adhering by brazing an orthodontic bracket or the like not illustrated onto the upper structure body 10, and connecting it to a predetermined tooth via an orthodontic wire, elastic, spring or the like.

Next, the constitution of an orthodontic implant structure 1 in accordance with the first embodiment shall be described.

As shown in FIG. 1 to FIG. 3B, the implant structure 1 consists of a pair of bolts 2A and 2B (2) that are used by embedding in a bone of the jaw in the mouth, a base plate 3 that is fixed to the head portion of each bolt 2 and supports the upper structure body 10, a first nut 4 (first screwing member) that screws onto a head thread portion 21 (described below) of each bolt 2, a second nut 5 (second screwing member) that screws onto a projecting thread portion 31 (described below) of the base plate 3, and the upper structure body 10 that is removable and provided on the base plate 3. The pair of bolts 2A and 2B are arranged in an approximately parallel manner while separated by a predetermined distance from each other.

Here, in the description of this implant structure 1, the distal end side of the bolts 2 in the axial direction shall be referred to as the "lower side" or "lower part", while the opposite side (base end side) shall be referred to as the "upper side" or "upper part".

As shown in FIG. 2, the upper structure body 10 is a thin plate that is left-right symmetrical as a whole, including a support portion 10a that is disposed in the middle and located at a position that is fixed to the implant structure 1 and main body plates 10b and 10c that extend in a wing shape from both sides of the support portion 10a in the horizontal direction via coupling portions 10d and 10d. An insertion hole 10e that can be fitted over a projecting thread portion 31 of a base plate 3 described below is formed in the support portion 10a. Note that the upper structure body 10 is constituted from a material such as stainless steel to which an orthodontic bracket or wire can be brazed for example.

As shown in FIG. 4, the bolt 2 for example is made of a material such as titanium or a titanium alloy and consists, in the following order from the head portion to the distal end in the axial line direction, of the head thread portion 21, a hexagonal locking portion 22 (locking portion) in which the cross-sectional shape being perpendicular to the axial direction is an angular shape, an engaging ring 23 (engaging portion) that has an outer shape being larger than the hexagonal locking portion 22, and an embedding thread portion 24 that has a thread on the outer circumference and is embedded in bone in the mouth.

The hexagonal locking portion 22 locks with a first locking hole 32 or a second locking hole 33 of the base plate 3 described below. A through hole 22a is provided in the hexagonal locking portion 22 in a direction perpendicular to the axial direction of the bolt 2. For example, rubber or wire that is fixed to a tooth to be moved is fixed to this through hole 22a by passing one end therethrough and the other end of this rubber or wire is fixed to the tooth, whereby it is possible to pull the tooth.

As shown in FIG. 2 and FIG. 4, the engaging ring 23 has a ring shape and is provided over the entire circumference of the bolt 2 in the circumferential direction, and the outer shape in plan view is larger than the outer shape of the embedding thread portion 24 and the hexagonal locking portion 22. For that reason, a lower surface 23a of the engaging ring 23 is disposed in a state of contacting with the membrane in the mouth (the chain double-dashed line H shown in FIG. 3B), while an upper surface 23b thereof supports the base plate 3.

The embedding thread portion 24 forms a spiral ridge portion across the entire axial direction on a cylindrical main body that has a pointed lower end. The bolt 2 is fixed by making it bite into the jaw bone by rotating the embedding thread portion 24, and in the state of the embedding thread portion 24 being embedded in the jaw, the portion upward from the engagement ring 23 (head thread portion 21 and the hexagonal locking portion 22) projects into the mouth.

As shown in FIG. 2, the base plate 3 is formed in an approximately rectangular flat shape in plan view, and is formed from a material such as stainless steel (titanium) for example. The specific constitution of the base plate 3 includes a projecting thread portion 31 in the center of the upper surface that projects upward and has a thread on its outer surface, and the first locking hole 32 and the second locking hole 33 that are formed on both sides of the projecting thread portion 31 so as to sandwich it and that respectively lock with the hexagonal locking portions 22 and 22 of the pair of bolts 2A and 2B.

The projection thread portion 31 is formed to be capable of passing through the insertion hole 10e of the upper structure body 10 mentioned. Around the base end portion in the projection thread portion 31, a seating face 3a for fixing the upper structure body 10 is formed. Also, on the base plate 3, guide portions 34 and 34 that extend in the short direction of the base plate 3 are formed on both sides of the seating face 3a so as to sandwich it. These guide portions 34 and 34 serve to restrict rotation of the upper structure body 10 that is attached to the projection thread portion 31 centered on the projection thread portion 31.

The inner circumference shape in plan view of the first locking hole 32 has a six-sided shape with the same cross-sectional shape as the hexagonal locking portion 22 of the bolt 2, and is formed to be capable of locking with the hexagonal locking portion 22.

The second locking hole 33 is an elongated hole with a six-sided shape in which the sides that extend parallel to the lengthwise direction of the base plate 3 (the axial line direction that passes through the centers of the pair of bolts 2A and 2B) are lengthened. That is, a structure is achieved in which, even in the case that the distance between the pair of bolts 2A and 2B is not fixed and even in the case that the pair of bolts 2A and 2B cannot be embedded in a mutually parallel state, by having one bolt 2 engaged with the first locking hole 32 and the other bolt 2 engaged with the second locking hole 33 within the range of the elongated hole, it is possible to attach the base plate 3. For example, assuming the minimum interval of the pair of bolts 2A and 2B is 7.8 mm, when the movement amount of the bolt 2 in the second locking hole 33 that forms the elongated hole is a range of 1.6 mm, the embedded interval of the pair of bolts 2A and 2B becomes 7.8 mm to 9.4 mm, and so if within this range, it is possible to embed the bolts 2A and 2B regardless of the mutual distance between the bolts 2A and 2B.

Here, with regard to the first nuts 4 shown in FIG. 2, that which corresponds to the bolt of reference numeral 2A is denoted by the reference numeral 4A, and similarly, that which corresponds to reference numeral 2B is denoted by reference numeral 4B.

In the state of the base plate 3 being arranged on the bolts 2, the first nuts 4A and 4B are screwed onto the head thread portion 21 of the respective bolts that projects upward from the base plate 3. Meanwhile, in the state that the projecting thread portion 31 of the base plate 3 fits the insertion hole 10e of the upper structure body 10, the second nut 5 is screwed onto the projecting thread portion 31 that projects upward from the upper structure body 10.

Next, the installation method using the implant structure 1 mentioned above and the action of the implant structure 1 will be described with reference to the drawings.

As shown in FIG. 2, first, an anchor position of the implant structure 1 (that is the embedding position of the bolts 2A and 2B) is determined with respect to the jawbone in the mouth of the patient having to undergo orthodontic treatment (for example, the central part of the palatal bone of the upper jaw). A special-purpose driver (not illustrated) is used to embed the two bolts 2A and 2B in the axial line direction of the bolts 2 while rotating them so as to be parallel with a predetermined interval.

Note that as shown in FIG. 3B, the downward screwing in of the bolts 2A and 2B to be embedded is completed at the position where the lower surface 23a of the engaging ring 23 (refer to FIG. 4) makes contact with the surface of the membrane (the chain double-dashed line H). At this time, since the engaging ring 23 is in a state of abutting the surface H of the membrane, it is possible to prevent the bolts 2A and 2B from sinking into the membrane.

Subsequently, the hexagonal locking portion 22 of the one bolt 2A that has been embedded is locked in the first locking hole 32 of the base plate 3 which is not the elongated hole, and the hexagonal locking portion 22 of the other bolt 2B is locked within the range of the second locking hole 33 that is the elongated hole. Therefore, for example, even if the distance between the pair of bolts 2A and 2B is in a state of not being constant or in a state of not being mutually parallel, since it is possible to dispose the base plate 3 on the pair of bolts 2A and 2B in the range of the elongated hole. Accordingly, work to embed the bolts at a high accuracy becomes unnecessary, and simplification of the work can be achieved.

By screwing the first nuts 4A and 4B onto the head thread portion 21 of each bolt, the base plate 3 is fixed. Note that even if the pair of bolts 2A and 2B that have been embedded are not parallel and in a state of being inclined slightly, since the base plate 3 is made of stainless steel or the like, the base plate 3 can be suitably curved, and the positions of the locking holes 32 and 33 can be adjusted to align with the hexagonal locking portions 22 and 23.

Then, after fitting the insertion hole 10e of the upper structure body 10 over the projecting thread portion 31, the second nut 5 is screwed onto the projecting thread portion 31 to fix the upper structure body 10. At this time, rotation of the upper structure body 10 that is fixed to the base plate 3 about the axis centered on the projecting thread portion 31 is restricted by the guide portions 34 and 34 (refer to FIG. 3A). The upper structure body 10 that is fixed is thus disposed in the state of the main body plates 10b and 10c being extended to both sides of the base plate 3.

Rotation with respect to the base plate 3 of the pair of bolts 2A and 2B that are embedded in this way is restricted since the hexagonal locking portions 22 and 22 have an angled shape and are made to lock with the first locking hole 32 and the second locking hole 33 of the base plate 3. Thereby, the pair of bolts 2A and 2B become firmly fixed without coming loose.

Since the upper structure body 10 can be detached from the base plate 3 by removing the second nut 5, when for example it is desired to move a tooth by puling it from a different direction, it is possible to perform straightening of a row of teeth by exchanging the upper structure with an upper structure body that has a different shape.

In the orthodontic implant structure in accordance with the first embodiment mentioned above, by locking the first locking hole 32 and the second locking hole 33 of the base plate 3 on the hexagonal locking portion 22 of the pair of bolts 2A and 2B, rotation of the bolts 2A and 2B is restricted. Therefore, the bolts 2A and 2B do not slip out and loosen, and it is possible to firmly fix the bolts 2A and 2B to a bone in the mouth. Furthermore, since the implanted bolts 2A and 2B do not wobble, it is possible to prevent the first nuts 4A and 4B that are screwed onto the head thread portion 21 from loosening. Moreover, since an implant structure that does not require a surgical operation, the bolts 2A and 2B can be readily embedded simply by screwing in with rotation.

Also, in this implant structure 1, it is possible to exchange only the upper structure body without removing the bolts 2A and 2B that have once been embedded. Accordingly, it is possible to exchange the upper structure body with a suitable upper structure body depending on the teeth straightening method such as changing the direction of pulling the teeth, and so it becomes possible to move teeth in various directions with respect to the teeth to be straightened, and suitable and reliable treatment can be carried out.

Next, an implant structure in accordance with a second embodiment of the present invention will be explained in detail with reference to FIG. 5 to FIG. 8. Note that those components and portions that are the same or similar as those of the first embodiment shall be denoted by the same reference numerals, overlapping descriptions should be omitted, and the characteristic portions should be described in detail.

Figure 5:
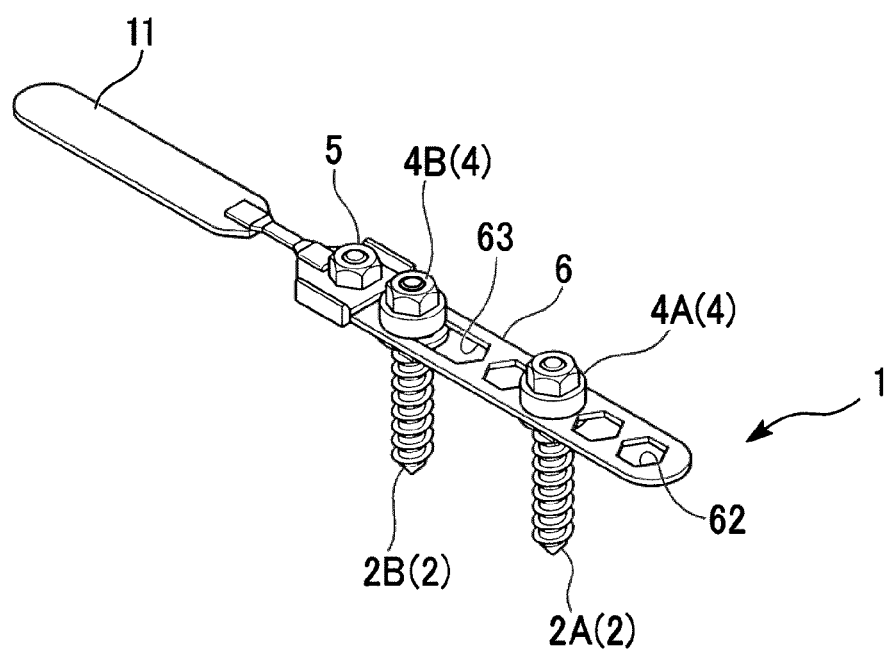
FIG. 5 is an outline perspective view of the implant structure in which an upper structure body in accordance with the second embodiment of the present invention is attached.
Figure 6:
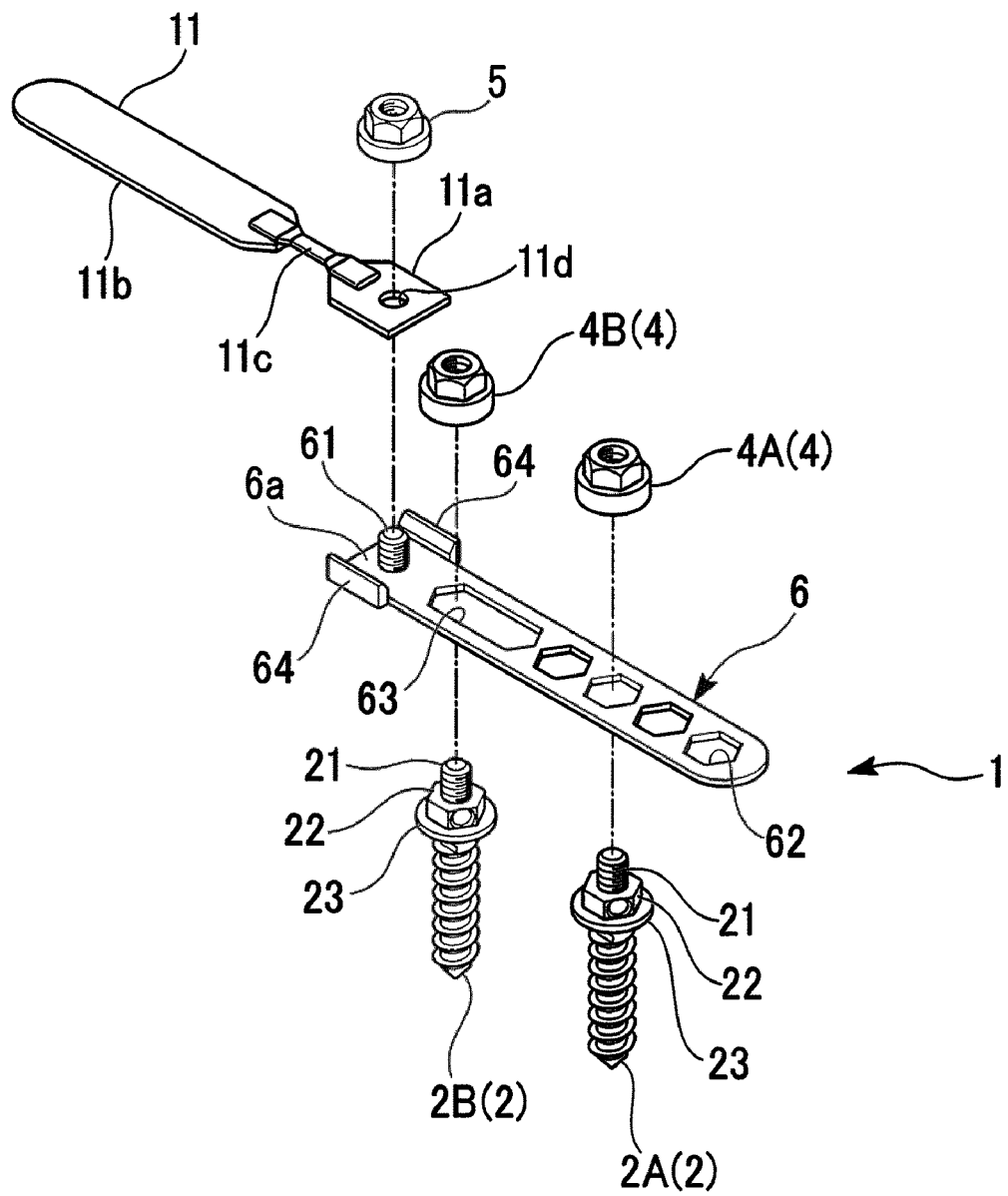
FIG. 6 is an exploded perspective view of the implant structure shown in FIG. 5.
Figure 7:
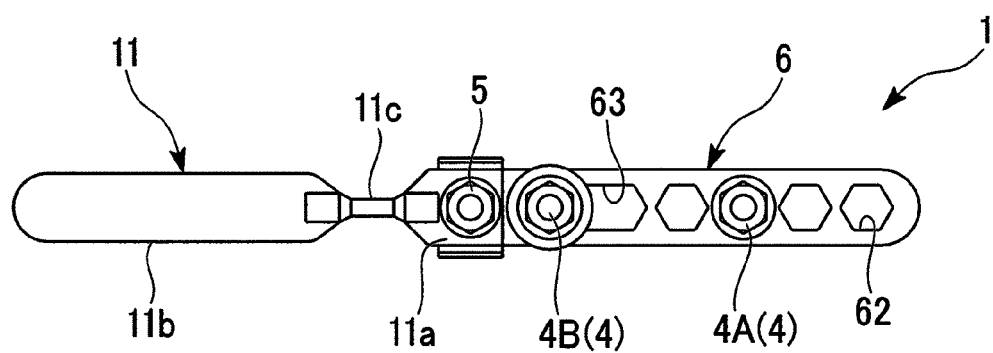
FIG. 7 is a plan view of the implant structure shown in FIG. 5.
Figure 8:
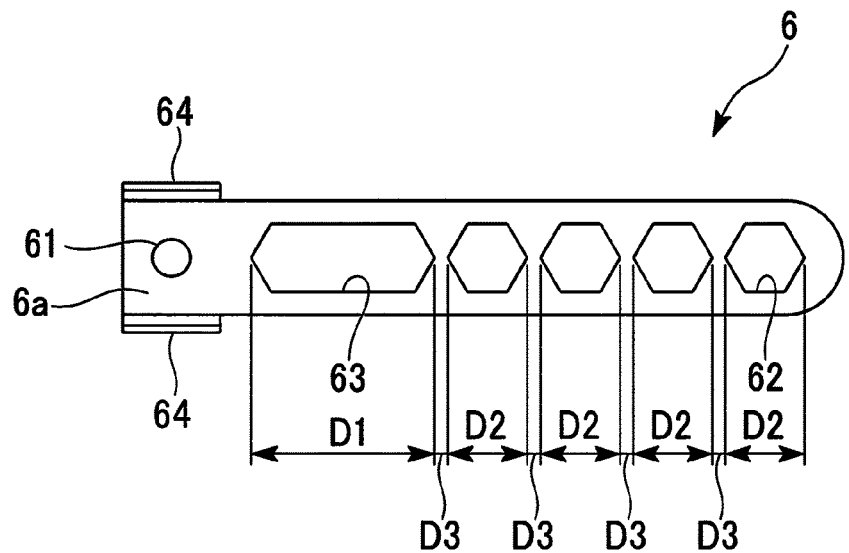
FIG. 8 is a plan view of the base plate that constitutes the implant structure shown in FIG. 5.

FIG. 5 is a perspective view that shows the outline of the implant structure in which the upper structure body is attached in accordance with the second embodiment of the present invention, FIG. 6 is an exploded perspective view of the implant structure shown in FIG. 5, FIG. 7 is a plan view of the implant structure shown in FIG. 5, and FIG. 8 is a plan view of the base plate of the implant structure shown in FIG. 6.

As shown in FIG. 5 and FIG. 6, in the implant structure in accordance with a second embodiment, instead of the base plate 3 of the first embodiment (as shown in FIG. 1), a plurality of first locking holes 62, 62, ... are provided, and a base plate 6 is used in which the position of mounting an upper structure body 11 (seating face 6a) is provided at one end in the lengthwise direction. For example, it is used by being fixed to any position of bone in the mouth.

As shown in FIG. 6 and FIG. 7, the upper structure body 11 that has one main body plate 11b is fixed to the base plate 6. Specifically, the upper structure body 11, instead of the upper structure body 10 (refer to FIG. 2) that provides the support portion 10a in approximately the center as in the first embodiment, has a support portion 11a in which an insertion hole 11d is formed at one end, and the plate-shaped main body plate 11b is fixed to this support portion 11a via a link portion 11c. The main body plate 11b consists of a material such as stainless steel and is constituted to be able to freely change the angle thereof by bending at the link portion 11c. In addition, the composition of the bolts 2A and 2B, the first nuts 4 and the second nut 5 are the same as in the first embodiment, so explanations thereof shall be omitted.

The base plate 6 is formed in an approximately rectangular flat shape in plan view, and has a projecting thread portion 61 that projects upward at one end thereof, a second locking hole 63 that is a long hole provided at a position on the side of the projecting thread portion 61, and a plurality of first locking holes 62, 62, ... (four in the second embodiment) that are arranged at an equal interval in the lengthwise direction at positions on the side opposite to the side of the projecting thread portion 61 so as to sandwich the second locking hole 63.

In the state of the main body plate 11b of the upper structure body 11 facing outward, after fitting the through hole 11d over the projecting thread portion 61 of the base plate 6, the second nut 5 is screwed onto the projecting thread portion 61, and the upper structure body 11 is thereby fixed to the implant structure 1 with respect to the base plate 6.

In the second embodiment, similarly to the first embodiment, one of the bolts 2A and 2B is engaged in any one of the plurality of first locking holes 62 of the base plate 6, and the other bolt 2 is engaged in the second locking hole 63.

As shown in FIG. 8, in the second embodiment, it is assumed for example that a length dimension D1 in the lengthwise direction of the second locking hole 63 is 5.6 mm, a length dimension D2 of the first locking holes 62 is 2.4 mm, and an interval D3 between adjacent first locking holes 62 and 62 and between the first locking hole 62 and the second locking hole 63 (locking hole interval dimension) is 0.4 mm. Specifically, the length dimension D1 of the second locking hole 63 is a dimension that sums the length of two of the first locking holes 62 and 62 and the dimension between the locking holes (D2+D2+D3), that is, is at least 5.2 mm. At this time, regarding the embeddable interval of the pair of bolts 2A and 2B, the minimum interval is 2.8 mm (that is, the distance between the centers of adjacent first locking holes 62 and 62), and the maximum interval is 14.4 mm. That is, if the embedding interval of the pair of bolts 2A and 2B to be embedded is in a range of 2.8 mm to 14.4 mm, it is possible to attach the base plate 6 to both bolts 2A and 2B.

In this way, in the second embodiment, since rotation of the bolts 2A and 2B is restricted similarly to the first embodiment, it is possible to improve the stability of the bolts 2A and 2B and possible to firmly fix them. Then, during attachment and detachment of the upper structure body 11, similarly to the first embodiment, it is possible to exchange it with an upper structure body having another shape simply by removing the second nut 5.

Next, modifications of the first embodiment (first through third modifications) will be described with reference to FIG. 9A to FIG. 9C.

Figure 9A:
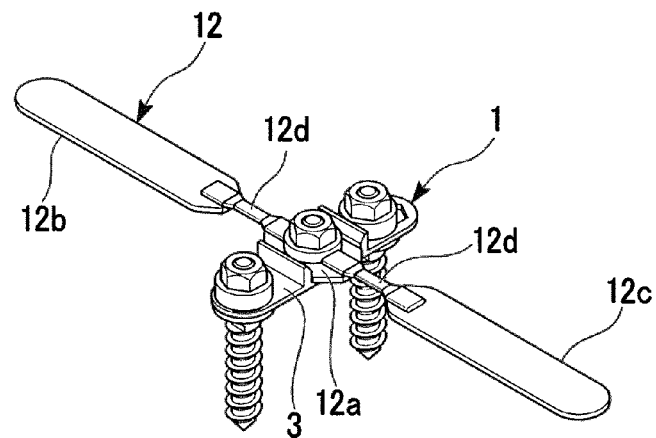
FIG. 9A is a perspective view that shows a modification of the first embodiment.
Figure 9B:
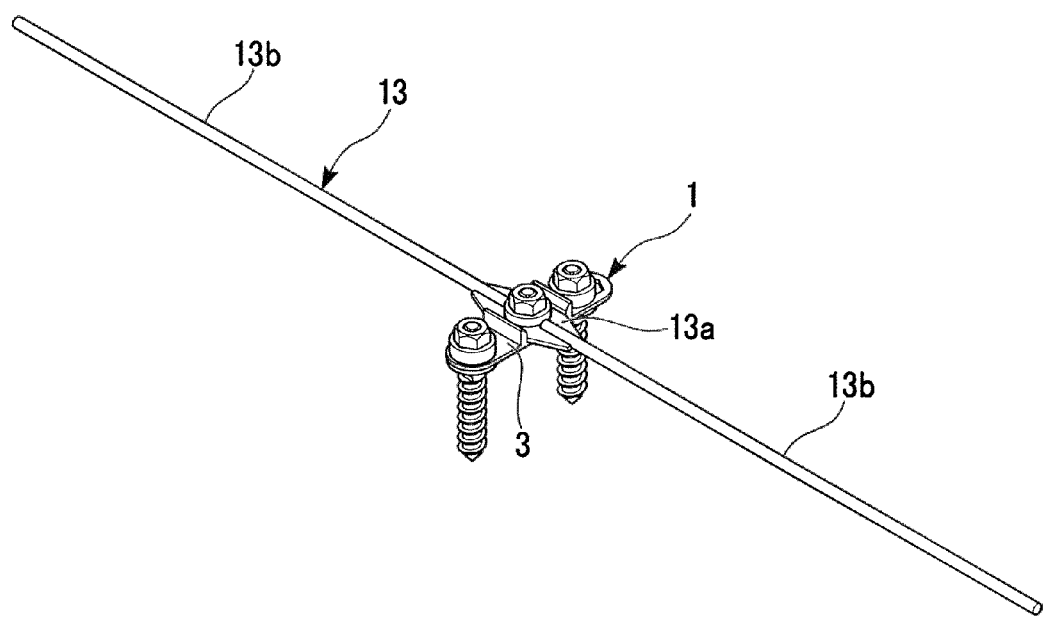
FIG. 9B is a perspective view that shows another modification of the first embodiment.
Figure 9C:
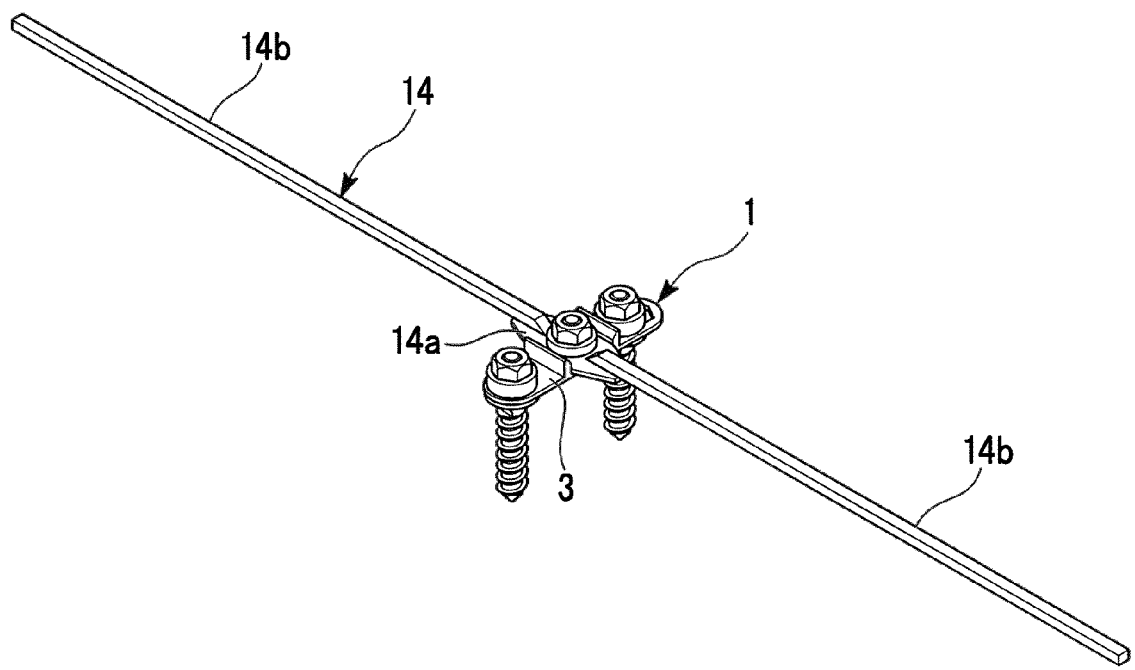
FIG. 9C is a perspective view that shows additional another modification of the first embodiment.

FIG. 9A to FIG. 9C are drawings that show other aspects of the first embodiment, being drawings corresponding to FIG. 1.

The first through third modifications shown in FIG. 9A to FIG. 9C show aspects that use an implant structure 1 similar to the first embodiment, that is, the base plate 3 that has the first locking hole 32 and the second locking hole 33 (refer to FIG. 2), while attaching differing upper structure bodies 12, 13 and 14, respectively, thereto.

As shown in FIG. 9A, the upper structure body 12 of the first modification provides main body plates 12b and 12c via link portions 12d and 12d on both sides from a support portion 12a that is provided in the middle. The main body plates 12b and 12c consist of a material such as stainless steel, and are constituted to be able to freely change the angle thereof by bending at will at the link portions 12d and 12d. Also, by brazing an orthodontic bracket, a wire is inserted in the bracket and movement of a tooth by the wire is possible.

As shown in FIG. 9B, in the upper structure body 13 of the second modification, round wires 13b and 13b having a round cross section are fixed in a manner extending from a support portion 13a located in the middle to both sides thereof.

As shown in FIG. 9C, in the upper structure body 14 of the third modification, square wires 14b and 14b having a square cross section are fixed in a manner extending from a support portion 14a located in the middle to both sides thereof.

Next, modifications of the second embodiment (fourth and fifth modifications) shall be described with reference to FIGS. 10A and 10B.

Figure 10A:
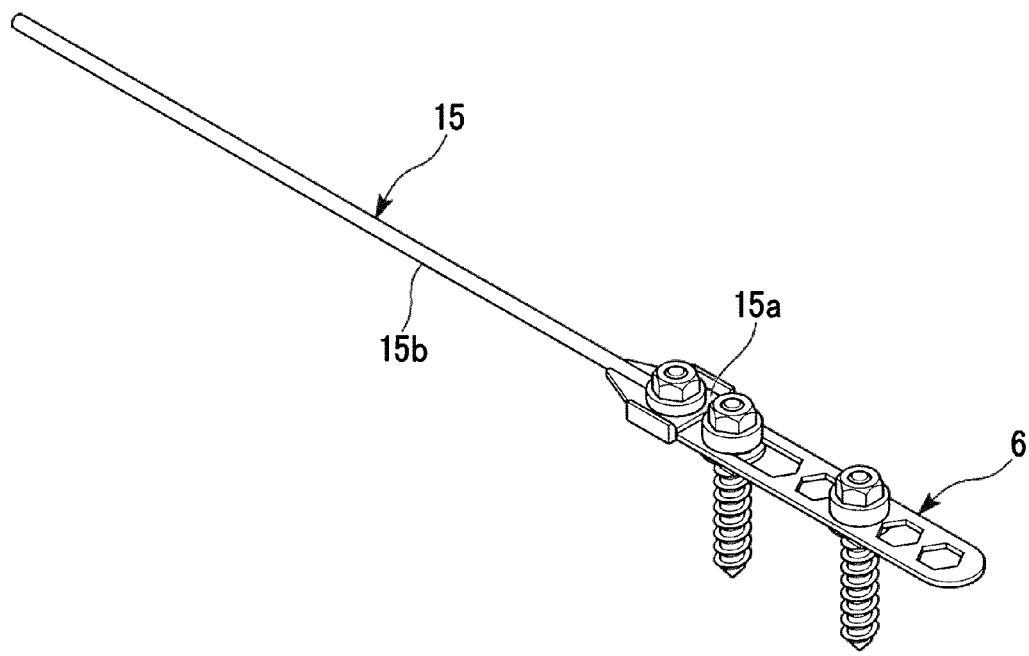
FIG. 10A is a perspective view that shows the second embodiment.
Figure 10B:
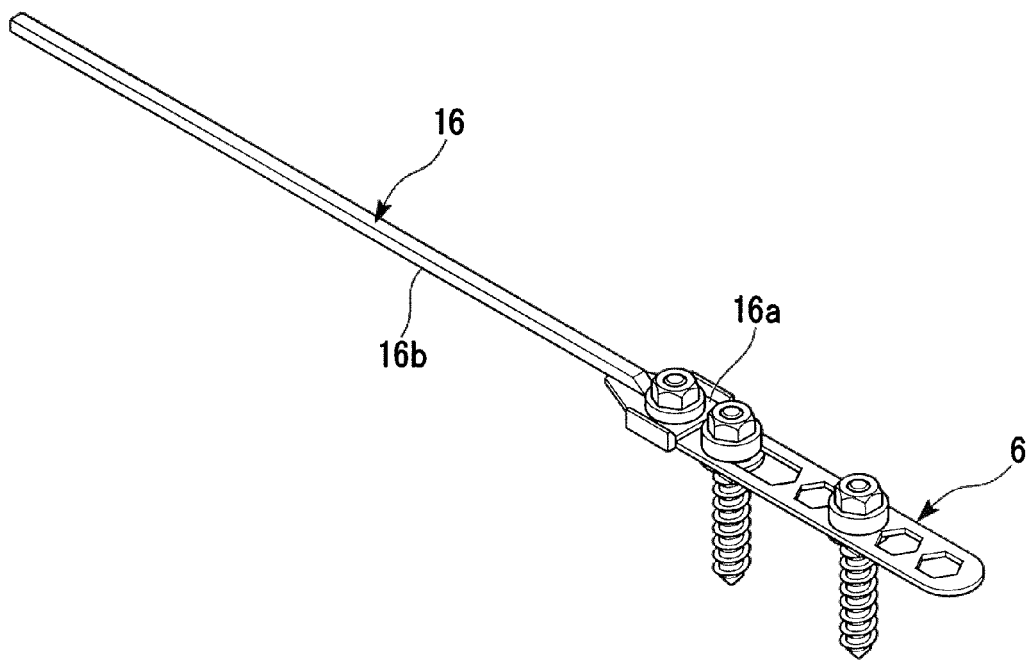
FIG. 10B is a perspective view that shows another modification of the second embodiment.

FIGS. 10A and 10B are drawings of other aspects of the second embodiment, being perspective drawings corresponding to FIG. 1.

In the fourth and fifth modifications shown in FIGS. 10A and 10B, aspects are shown that use a base plate 6 that has an implant structure 1 similar to the second embodiment (refer to FIG. 6), that is, has first locking holes 62, 62, . . . and a second locking hole 63, with respectively differing upper structure bodies 15 and 16 attached thereto.

As shown in FIG. 10A, in the upper structure body 15 of the fourth modification, a round wire 15b having a round cross section is fixed in a manner extending toward the outside from a support portion 15a that is located at one end.

As shown in FIG. 10B, in the upper structure body 16 of the fifth modification, a square wire 16b having a square cross section is fixed in a manner extending toward the outside from a support portion 16a that is located at one end.

The first embodiment, the second embodiment and modifications (first to fifth modifications) thereof of the orthodontic implant structure of the present invention were described hereinabove. However, the present invention is not limited to the above-mentioned embodiments and modifications, with appropriate modifications being allowed in a scope of not departing from the spirit or scope of the present invention.

For example, the embodiments included the hexagonal locking portion 22, but in plan view is not necessarily limited to a hexagonal shape. That is, provided it is angular in plan view, it may be triangular, square, octagonal or the like.

Also, the upper structure bodies 10 to 16, and the shape, length and kind of the base plate 3 are not necessarily limited to the embodiments and modifications.

Moreover, in the second embodiment and the fourth and fifth modifications, the number of the first locking holes 62 is four, but is not limited to this number, and one may be provided as in the case of the first locking hole 32 of the first embodiment, or three or five or more may be provided.

DESCRIPTION OF REFERENCE NUMERALS 1 implant structure
2, 2A, 2B bolt
3, 6 base plate
4, 4A, 4B first nut (first screwing member)
5 second nut (second screwing member)
10, 11, 12, 13, 14, 15, 16 upper structure body
10e, 11d insertion hole
21 head thread portion
22 hexagonal locking portion (locking portion)
23 engaging ring (engaging portion)
24 embedding thread portion
31, 61 projecting thread portion
32, 62 first locking hole
33, 63 second locking hole

The invention claimed is:

1. An orthodontic implant structure comprising:
an upper structure body (10-16) having a through hole (10e, 11d);
a pair of bolts (2, 2A, 2B) to be embedded in the jaw, of which each bolt having a head thread portion (21) provided at one end side in the lengthwise axial direction of the bolt, a locking portion (22), an engaging portion (23), and an embedding thread portion (24) at the other end side in the lengthwise axial direction of the bolt, in this order;
a base plate (3, 6) that has a projecting thread portion (31, 61) which can penetrate through the through hole (10e, 11d) and a first locking hole (32, 62) and a second locking hole (33, 63), with each of the first locking hole (32, 62) and the second locking hole (33, 63) capable of allowing penetration of the head thread portion (21) and the locking portion (22) of each bolt (2, 2A, 2B), not capable of allowing penetration of the engaging portion (23), and engageable with the locking portion (22) to block rotation of the locking portion (22) about the lengthwise axial line;
a first screwing member (4, 4A, 4B) that can be screwed onto either one of the head thread portions (21); and
a second screwing member (5) that can be screwed onto the projecting thread portion (31, 61),
wherein the second locking hole (33, 63) of the base plate (3) is an elongated hole that is longer in the lengthwise axial direction of the base plate (3) than the greatest dimension of the locking portion (22) of each bolt,
one of the locking portions (22) of the pair of bolts (2, 2A, 2B) is configured to be engageable with the first locking hole (32, 62) of the base plate (3),
the other of the locking portions (22) of the pair of bolts (2, 2A, 2B) is configured to be engageable with the second locking hole (33, 63) of the base plate (3) so as to be relatively movable in a lengthwise direction of the base plate (3),
the first screwing members (4, 4A, 4B) is screwed onto one of the head thread portions (21), and the through hole (10e, 11d) of the upper structure body (10-16) is fitted over the projecting thread portion (31) of the base plate (3), and the second screwing member (5) is screwed onto the projecting thread portion (31).

2. The orthodontic implant structure according to claim 1, wherein for at least one of the bolts the cross section of the locking portion (22) that is perpendicular to the lengthwise axial direction has a polygonal shape.

3. The orthodontic implant structure according to claim 2, wherein for at least one of the bolts the engaging portion (23) has a cross section of a size that can encompass the circumscribed circle of the polygonal shape of the locking portion (22).

4. The orthodontic implant structure according to claim 1, wherein the first locking hole (32, 62) has a hole cross-sectional shape that is complementary to the polygonal shape of the locking portion of each bolt (22).

5. The orthodontic implant structure according to claim 1, wherein the base plate (3) is formed in an approximately rectangular flat shape, and has a seating face (3a) configured to fix the upper structure body (10), and guide portions (34, 34), that the base plate (3), formed on opposite sides of the seating face (3a) so as to sandwich the seating face (3a).

* * * * *